United States Patent
Kerdar et al.

(10) Patent No.: US 7,998,503 B2
(45) Date of Patent: Aug. 16, 2011

(54) FORM OF ADMINISTRATION FOR CONTROLLING PRIMARY HEADACHES

(75) Inventors: Rasoul Sedaghat Kerdar, Aachen (DE); Maria Cristina Vázquez Lantes, Cologne (DE)

(73) Assignee: LTS Lohmann Therapie-Systeme AG (DE)

( * ) Notice: Subject to any disclaimer, the term of this patent is extended or adjusted under 35 U.S.C. 154(b) by 553 days.

(21) Appl. No.: 10/596,200

(22) PCT Filed: Dec. 13, 2004

(86) PCT No.: PCT/EP2004/014148
§ 371 (c)(1),
(2), (4) Date: Jun. 2, 2006

(87) PCT Pub. No.: WO2005/055977
PCT Pub. Date: Jun. 23, 2005

(65) Prior Publication Data
US 2007/0086955 A1    Apr. 19, 2007

(30) Foreign Application Priority Data
Dec. 12, 2003  (DE) ................. 103 58 749

(51) Int. Cl.
*A61K 9/70*       (2006.01)
*A61K 31/167*    (2006.01)
*A61K 47/38*     (2006.01)
*A61P 23/02*     (2006.01)
*A61P 25/06*     (2006.01)
*A61K 9/00*      (2006.01)

(52) U.S. Cl. ........ 424/443; 424/400; 514/626; 514/781; 514/818; 514/953

(58) Field of Classification Search .................. None
See application file for complete search history.

(56) References Cited

U.S. PATENT DOCUMENTS

| | | | |
|---|---|---|---|
| 5,120,544 | A | 6/1992 | Henley |
| 5,900,247 | A | 5/1999 | Rault et al. |
| 5,906,814 | A | 5/1999 | Epstein |
| 5,989,535 | A | 11/1999 | Nayak |
| 6,217,911 | B1 | 4/2001 | Vaughn et al. |
| 6,432,986 | B2 * | 8/2002 | Levin ............... 514/330 |
| 2002/0142036 | A1 | 10/2002 | Rupprecht et al. |

FOREIGN PATENT DOCUMENTS

| | | |
|---|---|---|
| DE | 696 22 980 | 12/1996 |
| DE | 100 35 865 | 2/2002 |
| DE | 101 46 251 | 4/2003 |
| WO | WO 97/11681 | 4/1997 |
| WO | WO 01/43733 | 6/2001 |
| WO | WO 01/66091 | 9/2001 |

OTHER PUBLICATIONS

Maizels et al, *Intranasal Lidocaine for Treatment of Migraine*, JAMA, Jul. 24-31, 1996—vol. 276, No. 4, pp. 319-321.
Abletshauser et al, XP 001205680, Herstellung und Untersuchung von isolierten MHPC-tannin-filmen; pp. 870-871, 1992.

* cited by examiner

*Primary Examiner* — Ernst Arnold
*Assistant Examiner* — Christopher R Lea
(74) *Attorney, Agent, or Firm* — Frommer Lawrence & Haug LLP

(57) ABSTRACT

The invention relates to a nasally applied, film-shaped, bioadhesive pharmaceutical form of administration containing at least one agent-containing layer that is based on crosslinked hydrophilic polymers comprising up to 60 percent by weight of Lidocaine, the percentage being in relation to the total quantity of crosslinked hydrophilic polymers. Also disclosed is the use thereof for controlling primary headaches, preferably migraine.

10 Claims, 1 Drawing Sheet

FORM OF ADMINISTRATION FOR CONTROLLING PRIMARY HEADACHES

The present invention relates to a bioadhesive pharmaceutical dosage form which can be administered nasally, is in film form, comprises at least one active ingredient-containing layer based on crosslinked hydrophilic polymers with up to 60% by weight, based on the total amount of crosslinked hydrophilic polymers, of lidocaine, and to the use of the active ingredient-containing layer for producing a monolayer or multilayer pharmaceutical dosage form which can be administered nasally for controlling primary headaches, especially migraine.

Headaches are differentiated into primary and secondary headaches. Whereas the pain associated with secondary headaches is only the consequence of another illness, primary headaches are a disorder per se. Accordingly, control of the headaches in this case is the actual aim of treatment.

Primary headaches may have various causes such as, for example, changes in the vascular system. The corresponding headaches are then referred to as neurovascular pain.

Neurovascular headaches which occur repeatedly and show preference for one side are also referred to as migraine.

Since an immediate effect is very particularly desired in the treatment of primary headaches in order to alleviate the pain, dosage forms particularly suitable therefor are those guaranteeing a rapid delivery of active ingredient into the circulation. Oral dosage forms such as tablets or capsules are, however, not the first choice therefor; on the contrary inter alia nasal administration by which rapid alleviation of primary headaches, especially migraine, can be achieved.

To the extent that WO 01/43733 describes transmucosal administration of active ingredients through the nasal mucosa for controlling headaches, dosage forms with only lidocaine as sole active ingredient are assessed as unsuitable.

It is further known from the prior art that although lidocaine leads, after nasal administration, e.g. in the form of sprays, to a rapid alleviation of migraine pain, this pain flares up again after a short time. The publication of Maizels et al., Journal of the American Medical Association (1996, July), 276(4), pages 319-321, confirms that nasally administered lidocaine leads to a fast decline in migraine pain. On the other hand, recurrence, meaning renewed appearance of the pain, was found shortly after administration of lidocaine.

In order to control this renewed appearance of pain, especially migraine pain, continued administration of lidocaine, in particular a continued nasal administration of lidocaine, is desirable.

It was therefore an object of the present invention to provide a dosage form which ensures both accurate dosage and continuous delivery of lidocaine over several hours via the nasal mucosa for controlling headaches, especially migraine pain in humans, the intention being that both immediate control of pain and the control of pain which flares up again, i.e. occurs repeatedly, or continuous pain, and simple administration of the dosage form, preferably as single administration form, should be possible by one and the same dosage form.

This object is achieved by providing a bioadhesive, monolayer or multilayer pharmaceutical dosage form which can be administered nasally, is in film form and has at least one active ingredient-containing layer based on crosslinked hydrophilic polymers with up to 60% by weight of lidocaine, based on the total amount of crosslinked hydrophilic polymers.

The high loading with up to 60% by weight of lidocaine in at least one of the active ingredient-containing layers of the dosage form of the invention was not to be expected because other film-forming polymers such as, for example, ethylcellulose allow a loading of only up to about 25% by weight of active ingredient. An active ingredient concentration going beyond this usually leads to crystallization thereof. Crystallization causes brittle films which do not ensure sufficiently safe handling inter alia on administration. In addition, the films are cloudy, thus impairing acceptance by the patients.

The selection according to the invention of crosslinked hydrophilic polymers as film-forming substances for the active ingredient-containing layer, which are preferably crosslinked during or after the loading with lidocaine provide lidocaine-containing layers with a proportion of up to 60% by weight of lidocaine, based on the total amount of crosslinked hydrophilic polymers, preferably from 20 to 55% by weight and particularly preferably from 30 to 50% by weight.

It is additionally possible by embodying the claimed dosage form as film to ensure reliable and accurate dosage. It is possible at any time to check whether the dosage form adheres to the nasal mucosa. In addition, it is possible at the end of the therapy for the dosage form to be removed again without active ingredient.

The crosslinking of the film-forming, active ingredient-containing, hydrophilic polymers preferably takes place during the formation of the layer, i.e. in situ, with the aid of known crosslinkers, preferably phenolic crosslinkers and/or polyacrylic acid derivatives, particularly preferably with tannin and/or polycarbophil (homopolymers of acrylic acids crosslinked with divinylglycol, optionally neutralized with calcium). The ratio of hydrophilic polymers to crosslinker is preferably from 2:1 to 5:1, particularly preferably 4:1, by weight.

The crosslinking of the film-forming polymers makes it possible, despite the high lidocaine loading, to ensure sufficiently safe handling of the dosage form, e.g. on removal from the package and introduction into the nose, without damage to the dosage form through tearing. The crosslinking makes it possible according to the invention to provide dosage forms having a minimum tear strength of 40 N, preferably of at least 50 N, particularly preferably of at least 60 N, despite a high lidocaine concentration.

Hydrophilic polymers preferably employed for the dosage form of the invention are water-soluble cellulose ethers, particularly preferably hydroxyethylcellulose, methylcellulose, hydroxypropylcellulose and/or hydroxypropylmethylcellulose, very particularly preferably hydroxypropylmethylcellulose.

The dosage forms of the invention may be monolayer or multilayer. If the dosage forms are multilayer, they may have more than one active ingredient-containing layer and/or a covering layer and/or an adhesive layer.

The lidocaine release from the active ingredient-containing layer or from the further active ingredient-containing layers which are present can be controlled not only via the difference in lidocaine concentration but also via the degree of crosslinking of the hydrophilic polymers. It is possible for example to control the release via a lidocaine concentration gradient within a lidocaine-containing layer. A further possibility for influencing the lidocaine release consists of providing a plurality of lidocaine-containing layers with different lidocaine concentrations in the dosage forms of the invention. It is also possible for active ingredient-free layers, where appropriate composed of crosslinked hydrophilic polymers, to be present between the active ingredient-containing layers. It is thus possible for the active ingredient to be released rapidly and in a sufficient amount for immediate control of pain from one active ingredient-containing layer, while a longer-lasting lidocaine release is achieved from further active ingredient-containing layers in order to make sustained pain control possible.

The active ingredient-containing layer preferably has a thickness of 30-500 μm.

In order to ensure adequate adhesion of the dosage form of the invention on nasal administration, it is possible either to incorporate a bioadhesive polymer into the lidocaine-containing layer, or to provide an additional layer as adhesive layer in the dosage form of the invention. An adhesive layer may consist of one or more of the known bioadhesive polymers such as, for example, polyacrylic acid derivatives. The adhesive layer may consist for example of a mixture of optionally crosslinked hydrophilic polymers and a polyacrylic acid derivative or only of polyacrylic acid derivatives. Suitable bioadhesive polyacrylic acid derivatives are polyacrylic acids which are optionally partly in the form of the calcium salt and are optionally crosslinked. Polyacrylic acids which are partly in the form of the calcium salt and are crosslinked with divinylglycol are particularly preferred. Such products are marketed as polycarbophils®.

The adhesive layer may also consist of a mixture of one or more of said bioadhesive polymers and of one or more non-bioadhesive polymers such as, for example, ethylcellulose, especially if additional control of active ingredient release with the aid of the adhesive layer is desired.

The adhesive layer preferably has a thickness of from 10 to 100 μm.

The dosage form of the invention preferably also has a covering layer. The covering layer preferably consists of a water-insoluble polymer and is impermeable for the active ingredient lidocaine. Unidirectional active ingredient release is ensured thereby. With this unidirectional release, the active ingredient is delivered only to the nasal mucosa.

The covering layer may be composed of crosslinked hydrophilic polymers, for example of hydroxypropyl-methylcellulose crosslinked with tannin.

It is also possible for the covering layer to be composed of at least one water-insoluble cellulose ether, preferably of alkylcellulose, particularly preferably of ethylcellulose, or one water-insoluble cellulose ester, preferably cellulose acetate, and/or one water-insoluble poly(meth)acrylate, preferably a poly(C1-4)-alkyl(meth)acrylate, poly(C1-4)-dialkyl-amino-(C1-4)-alkyl(meth)acrylate and/or copolymers thereof, very particularly preferably one copolymer of ethyl acrylate/methyl methacrylate and/or one copolymer of ethyl acrylate/methyl methacrylate/trimethyl-ammoniumethyl methacrylate chloride. Where appropriate, the cellulose ethers, the cellulose esters and the poly(meth)acrylates may comprise plasticizers.

The covering layer preferably has a thickness of from 10 to 100 μm.

In a preferred embodiment of the claimed invention, the covering layer is of ethylcellulose or of a copolymer of ethyl acrylate/methyl methacrylate/trimethyl-ammoniumethyl methacrylate chloride with a molar ratio of the respective monomers of 1:2:0.1, in both cases with a percentage amount of plasticizer, preferably triethyl citrates, of from 20 to 40% by weight, based on the amount of the polymer. A very particularly preferred covering layer consists of a copolymer of ethyl acrylate/methyl methacrylate with a molar ratio of the respective monomers of 2:1, with addition of plasticizer not being absolutely necessary.

To protect the dosage form of the invention it is also possible for it to be covered before administration with a protective layer, e.g. a plastics sheet or aluminum sheet.

The dosage form of the invention is particularly suitable, because of the high lidocaine loading, for controlling primary headaches in humans.

The present invention then further relates to the use of at least one lidocaine-containing layer in film form based on crosslinked hydrophilic polymers with up to 60% by weight of lidocaine, based on the total amount of crosslinked hydrophilic polymers, for producing a pharmaceutical dosage form which can be administered nasally for controlling primary headaches, preferably neurovascular headaches, particularly preferably for treating migraine in humans.

The dosage form of the invention is preferably produced by forming the active ingredient-containing layer or active ingredient-containing layers, preferably from an aqueous solution of the hydrophilic polymers and of lidocaine by application with simultaneous or subsequent exposure to the crosslinker, preferably by in situ crosslinking and preferably as an aqueous solution, and removal of the water by drying.

The covering layer can be produced by applying an aqueous dispersion such as a latex or pseudolatex dispersion of a water-insoluble polymer or a solution of such a polymer in a suitable organic solvent to the dried active ingredient-containing layer, with subsequent removal of the water or organic solvent by drying and/or vacuum treatment.

If an adhesive layer is present on the dosage form of the invention, this is preferably produced like the active ingredient-containing layers.

The dosage form of the invention is preferably produced by assembling the individual layers one on top of the other on a smooth surface, applying the respective film-forming polymer together with the optionally present crosslinker and the optionally present active ingredient for each layer, in each case by spraying and drying as partial layers. The drying takes place in this case preferably simultaneously with the spraying. The partial layers preferably each have a thickness of from 0.1 to 10 μm.

The spraying of the aqueous solution of the hydrophilic polymers and of the aqueous solution of the crosslinker preferably takes place simultaneously, in which case the hydrophilic polymers and the crosslinker mix after the spraying and then the polymer is crosslinked in situ.

If the active ingredient lidocaine is present in one layer, the loading preferably takes place by the lidocaine already being dissolved in the aqueous solution of the hydrophilic polymers before this solution is brought into contact with the solution of the crosslinker.

The great variability of this procedure allows the layers to be assembled in any sequence. It is thus possible to form first the adhesive layer or first the covering layer as basis for the subsequent layers.

An apparatus as described in DE 101 46 251 is preferably employed for carrying out the production process. The corresponding disclosure is incorporated in the present disclosure.

This apparatus comprises at least one spraying device, a dryer and at least one plate which is moved cyclically through underneath the spraying device. The apparatus preferably has a plurality of nozzles whose spray cones overlap.

Method for Determining the Tear Strength

A TA.XT2i texture analyzer from Winopal (Germany) is employed to determine the tear strength. Pieces of film of the dosage form of the invention with a length of 9.5 cm and a width of 1 cm are clamped at both ends with clamping jaws and slightly stretched so that the free tension length is 7 cm. The clamping jaws are provided with coatings on the surface which come into contact with the pieces in order to avoid premature tearing of the pieces at the clamps. If a piece tears despite coatings on the clamps, these values are not taken into account. The upper clamp pulls upwards at a constant speed of 0.5 mm/s. The force employed at every time during this, and the resulting extension, is recorded by the texture analyzer. The force, the extension and the time are then displayed and analyzed with the aid of software.

The tear strength of an investigated piece of film is the force acting on the piece of film just at the moment when the particular piece tears.

Figure 1:
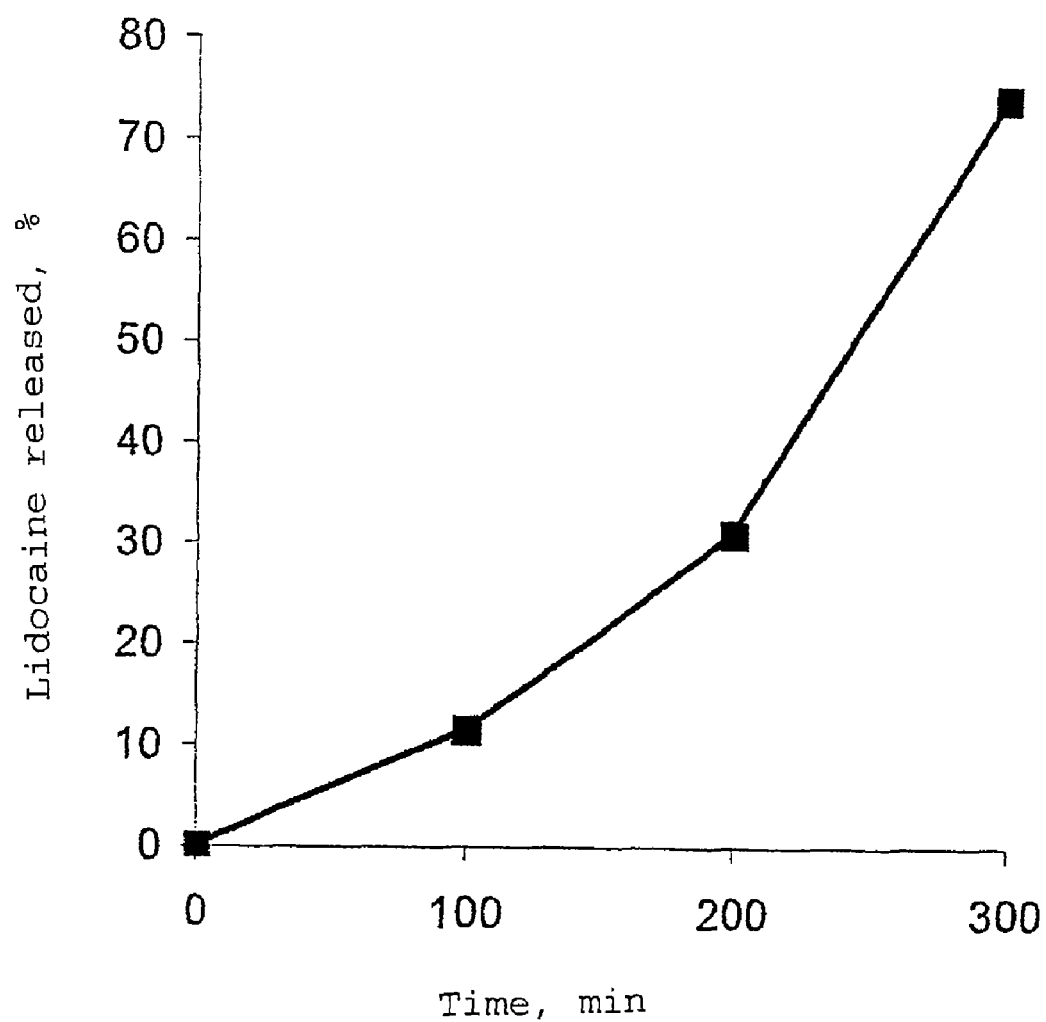
FIG. 1 depicts the lidocaine release from the dosage form of Example 4.

EXAMPLE 1 a) The covering layer was produced by preparing a solution of 10 g of hydroxypropylmethylcellulose and 490 g of water, and a solution of 2.5 g of tannin in 497.5 g of water. These two solutions were sprayed, using nozzles in each case, with the aid of the apparatus described in DE 101 46 251 simultaneously onto a glass plate and dried at 80° C., and the spraying process was repeated after formation of the respective partial layer a plurality of times until a layer thickness of 100 μm had been reached.
b) In the same manner as described in a), a solution of 10 g of hydroxypropylmethylcellulose, 6.25 g of lidocaine and 490 g of water, and a solution of 2.5 g of tannin in 497.5 g of water was applied with the aid of the same apparatus in partial layers by a multiple spraying process on the covering layer until a layer thickness of 300 μm had been reached. Lidocaine loading in the active ingredient-containing layer was 50% by weight.
c) A dispersion of 6 g of polyacrylic acid cross-linked with divinylglycol (polycarbophil®) in 494 g of water was prepared. This dispersion was also with the aid of the apparatus indicated above in a multiple spraying process in which the partial layers were produced in each case, until the adhesive layer had reached a layer thickness of 50 μm.

The dosage form produced in this way was flexible and easily handled.

EXAMPLE 2

A dosage form of the invention was produced as described in Example 1, with the difference that a solution of 333.33 g of a 30% strength aqueous latex of an ethyl acrylate/methyl methacrylate copolymer with a molar ratio of the monomers of 1:1 in 666.67 g of water was used to produce the covering layer in a). The layer thickness of the covering layer was applied, different from the covering layer in Example 1 a), only up to a thickness of 50 μm. The dosage form produced in this way here was flexible and easily handled.

EXAMPLE 3

A dosage form of the invention was produced as described in Example 1, with the difference that 7.5 g of lidocaine was used to produce the active ingredient-containing layer in b). Lidocaine loading in the active ingredient-containing layer was 60%.

The dosage form produced in this way was flexible and easily handled.

EXAMPLE 4 a) The active ingredient-containing layer with a concentration gradient from 8% by weight to 50% by weight and with a lidocaine loading of 35% was produced by preparing three solutions: a first solution of 0.6 g of lidocaine, 6 g of hydroxy-propylmethylcellulose and 294 g of water, a second solution of 7.5 g of lidocaine, 10 g of hydroxypropylmethylcellulose and 490 g of water, and a third solution of 2.5 g of tannin and 497.5 g of water. With the aid of the apparatus described in DE 101 46 251, the first and the third solution were sprayed simultaneously onto a glass plate, with the second solution being added continuously to the first solution, so that the volume of the first solution remained constant during the spraying process, and the concentration rose continuously. Drying was carried out at 80° C. The spraying process terminated when the second and the third solutions were completely consumed. The first solution remained and, at the end of the spraying process, still contained 3.77 g of lidocaine and 6 g of hydroxypropylmethylcellulose. The active ingredient-containing layer had a layer thickness of 250 μm.
b) The covering layer was produced by using a solution of 333.33 g of a 30% strength aqueous latex of an ethyl acrylate/methyl methacrylate copolymer with a molar ratio of the monomers of 1:1 in 666.67 g of water. The covering layer was applied until the thickness was 50 μm.

The dosage form produced in this way here was flexible and easily handled. The lidocaine release from this dosage form is depicted in FIG. 1 (the release was carried out with the aid of the apparatus described in German patent application 102 24 518.5, with the flow rate in the measuring cell being 1 ml/min).

The invention claimed is:

1. A monolayer bioadhesive pharmaceutical dosage form which can be administered nasally and is in film form, comprising a lidocaine containing layer based on crosslinked hydrophilic polymers from 50% by weight to 60% by weight of lidocaine, based on the total amount of crosslinked hydrophilic polymers,
   wherein the dosage form has a tear strength of at least 40 N and
   the hydrophilic polymer of the active ingredient-containing layer has been crosslinked in situ and the ratio of hydrophilic polymers to crosslinker is from 2:1 to 5:1 by weight and
   wherein the lidocaine-containing layer is also an adhesive layer.

2. The dosage form as claimed in claim 1, characterized in that the dosage form has a tear strength, of at least 50 N.

3. The dosage form as claimed in claim 1, characterized in that a cellulose ether has been used as hydrophilic polymer.

4. The dosage form as claimed in claim 3, characterized in that the cellulose ether is selected from the group consisting of hydroxyethylcellulose, methylcellulose, hydroxypropylcellulose and hydroxypropylmethylcellulose.

5. The dosage form as claimed in claim 1, characterized in that the dosage form has a tear strength of at least 60 N.

6. The dosage form as claimed in claim 5, characterized in that the hydrophilic polymer is a cellulose ether and the cellulose ether is selected from the group consisting of hydroxyethylcellulose, methylcellulose, hydroxypropylcellulose and hydroxypropylmethylcellulose.

7. The dosage form as claimed in claim 1, characterized in that the dosage form exhibits controlled release of lidocaine.

8. A method for controlling primary headaches in humans which comprises of administering a therapeutically effective amount of the bioadhesive pharmaceutical dosage form of claim 1.

9. The method of claim 8, wherein the control of primary headaches is via controlling neurovascular pain.

10. The method of claim 8, wherein the control of primary headaches is reduces the effect of a migraine.

* * * * *